US012127962B2

(12) United States Patent
DiGiovanni et al.

(10) Patent No.: US 12,127,962 B2
(45) Date of Patent: Oct. 29, 2024

(54) PLANTAR FASCIITIS RECOVERY DEVICE

(71) Applicant: Medi-Dyne Healthcare Products, Ltd., Collyville, TX (US)

(72) Inventors: Craig DiGiovanni, Collyville, TX (US); Andrew Sawyers, Hurst, TX (US)

(73) Assignee: Medi-Dyne Healthcare Products, Ltd., Collyville, TX (US)

( * ) Notice: Subject to any disclaimer, the term of this patent is extended or adjusted under 35 U.S.C. 154(b) by 589 days.

(21) Appl. No.: 16/201,326

(22) Filed: Nov. 27, 2018

(65) Prior Publication Data
US 2019/0159920 A1   May 30, 2019

Related U.S. Application Data

(60) Provisional application No. 62/590,758, filed on Nov. 27, 2017.

(51) Int. Cl.
*A61F 5/01*   (2006.01)
*A61F 5/37*   (2006.01)

(52) U.S. Cl.
CPC ........... *A61F 5/0111* (2013.01); *A61F 5/3715* (2013.01)

(58) Field of Classification Search
CPC .... A61F 5/0113; A61F 5/0111; A61F 5/3715; A61F 2005/0197; A61F 5/0109; A61F 5/0127; A61F 5/019; A61F 5/05841; A61F 5/0585; A41B 11/0006; A41B 11/02; A41D 13/06; Y10S 482/907
USPC ........... 602/28; 482/124; 2/239; 36/164, 165
See application file for complete search history.

(56) References Cited

U.S. PATENT DOCUMENTS

| 5,399,155 | A | * | 3/1995 | Strassburg | A61F 5/0111 2/239 |
| 5,776,090 | A | * | 7/1998 | Bergmann | A61F 5/0111 128/882 |
| 7,806,844 | B2 | * | 10/2010 | Outred | A61F 5/0113 602/5 |
| 7,896,784 | B2 | * | 3/2011 | Campbell | A63B 21/0023 482/907 |
| 2007/0100268 | A1 | * | 5/2007 | Fisher | A61F 5/0113 602/28 |
| 2010/0256544 | A1 | * | 10/2010 | Colon | A61F 5/05 602/28 |
| 2011/0172578 | A1 | * | 7/2011 | Chiu | A61F 5/0127 602/28 |
| 2015/0190263 | A1 | * | 7/2015 | Szczepanski | A61F 5/0127 602/28 |
| 2015/0265450 | A1 | * | 9/2015 | Rodgers | A61H 1/0266 601/84 |
| 2015/0335460 | A1 | * | 11/2015 | Weaver, II | A61F 5/14 602/7 |

(Continued)

*Primary Examiner* — Keri J Nelson
(74) *Attorney, Agent, or Firm* — Sheri Higgins; Sheri Higgins Law, PLLC

(57) ABSTRACT

A sock device comprising: a first anchor; a sock; a strap, wherein the strap removably secures the first anchor to the sock; and a distributor. The strap can be used to fit through an attachment ring on the first anchor, pulled down towards a user's ankle, and secured to the sock thereby providing temporary flexion to the foot, which stretches the muscles and tendons of the heel region, calf region, and underneath area of the feet to help treat plantar fasciitis. The distributor provides an even distribution of flexion to the entire width of the foot.

18 Claims, 4 Drawing Sheets

(56) References Cited

U.S. PATENT DOCUMENTS

2018/0333285 A1* 11/2018 Thor ................. A43B 7/20

* cited by examiner

PLANTAR FASCIITIS RECOVERY DEVICE

TECHNICAL FIELD

A device for the treatment, recovery, or prevention for plantar fasciitis can include a means for stretching the muscles and tendons of the heel region, calf region, and underneath area of the feet.

BRIEF DESCRIPTION OF THE FIGURES

The features and advantages of certain embodiments will be more readily appreciated when considered in conjunction with the accompanying figures. The figures are not to be construed as limiting any of the preferred embodiments.

DETAILED DESCRIPTION

Plantar fasciitis is one of the most common causes of heel pain. It involves inflammation of a thick band of tissue that runs across the bottom of your foot and connects your heel bone to your toes (plantar fascia). Plantar fasciitis pain usually develops gradually, but it may feel as though it has happened quite suddenly. Occasionally, a person will feel a quick burst of pain right after missing a step or jumping down from a height. While plantar fasciitis can happen at any age, 90% of the cases of plantar fasciitis pain occur after the age of 40. This is because the fascia loses some of its normal elasticity and resilience with aging and then can more easily become irritated with routine daily activities. There are a variety of factors that can contribute to such a development, including for example, flat feet, high arches, rigid feet, inadequate shoe support, age, sudden weight increase, sudden increase in activity, after a return from a period of inactivity, and family history.

Many times, sufferers of plantar fasciitis pain describe the pain as coming from under the heel and on the inside, at the origin of the attachment of the fascia. There can be pain when pressing on the inside of the heel and sometimes along the arch. Frequently, patients describe the plantar fasciitis pain as being worse first thing in the morning as the fascia tightens up overnight and then the pain might ease some after a few minutes as the foot gets warmed up. This is sometimes referred to as "first-step pain".

Several techniques have been developed to aid in the treatment, recovery, and prevention of plantar fasciitis. Some common techniques include rest, medication (including steroids), physical therapy including stretching, and surgical removal of the heel spur. Some devices are currently available that stretch the muscles in an effort to help alleviate the pain associated with plantar fasciitis; however, these devices do not provide a uniform distribution of tension that allows stretching of the muscles in a consistent and thorough manner. Thus, there is a need and an ongoing industry-wide concern for devices that can help relieve the pain and assist other techniques being used for the treatment, recovery, and prevention of plantar fasciitis.

It has been discovered that a sock device that stretches the muscles and tendons of the heel region, calf region, and underneath area of the feet can be used to treat plantar fasciitis. The sock device can be worn at night while sleeping and even worn throughout the day in a continuous fashion or periodically as needed. The sock device can include a distributor to provides an evenly distributed tension to the toe regions of the feet whereby this even distribution of tension provides a uniform and thorough stretching of all of the muscles associated with plantar fasciitis as opposed to an uneven distribution of tension, which can result in only some of the necessary muscles being stretched.

Figure 1:
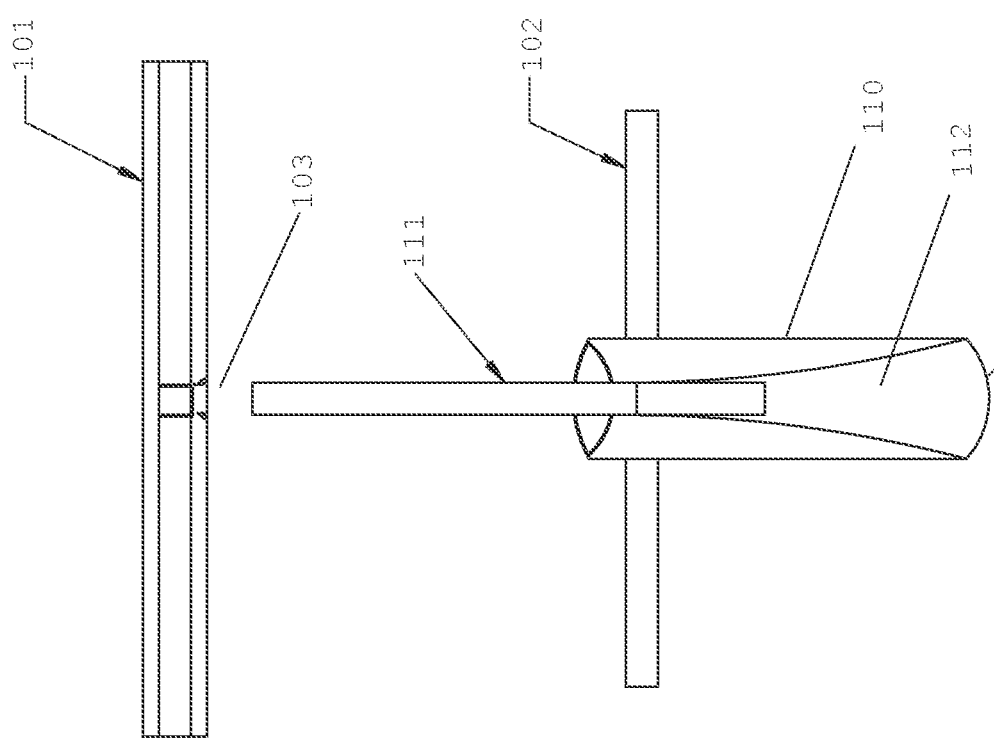
FIG. 1 is a top view of a sock device according to certain embodiments.

FIG. 1 is an illustration of a sock device 100 according to certain embodiments. The sock device 100 can include a first anchor 101, which can consist of an adjustable strap that can be positioned around the circumference of a user's lower leg at a location below the knee and above the major portion of the calf muscle. The adjustable strap can be secured around the user's lower leg via wrapping a first end and second end of the strap around the lower leg and then attaching the first end to the second end. Preferably, after the adjustable strap is secured to the lower leg, the strap remains substantially in the same location where the strap was secured without substantial movement or the first and second ends becoming separated with normal movement.

The adjustable strap can be adjusted and removably attached around the user's lower leg, for example, via VELCRO®; or a hook that is located on the first end of the strap and a plurality of eyes positioned in a desired spacing pattern located along the second end of the strap. By way of example, the hook can be positioned on an underneath side (i.e., the side that would be closest to the skin of the user) of the first end of the strap, while the plurality of eyes can be positioned on an upper side (i.e., the side that would not be in contact with the user's skin) along the second end of the strap. Without limitation, the eyes can number between 3 to 10 and can be spaced apart at a distance in the range of about 0.5 inches (1.3 centimeters) to about 1.5 in (3.8 cm). By way of another example, the first end of the strap can include a button hole and the second end of the strap can include a plurality of buttons as described above with reference to the eyes. By way of yet another example, snap fasteners can be used to removably attach the adjustable strap. According to this embodiment, a male snap having a protrusion or circular lip can be on the first end while a plurality of female snaps having a groove for receiving the protrusion can be located along the second end similar to the buttons or eyes. Preferably, the length of the adjustable strap as well as the number and spacing of the eyes or buttons are selected such that the adjustable strap can accommodate a variety of user's lower leg circumferences. By way of example, the adjustable strap can be designed to accommodate user's lower leg circumference in the range of about 10 in to about 22 in (about 25.4 cm to about 55.9 cm). As used herein, "accommodate" means that the adjustable strap can be positioned entirely around the circumference of the user's lower leg and the first and second ends of the strap can be secured to one another such that the adjustable strap is secured to the user's lower leg. In this manner, the user can position the adjustable strap around the circumference of the lower leg and attach the first end to the second end. The user may then wear the sock device 100 for a desired period of time. When the user no longer desires to wear the sock device 100, then the user may release the first end from attachment to the second end.

The first anchor 101 can include an attachment ring 103 that can be positioned in line with the middle of a user's patella, also known as a knee cap. The attachment ring 103 can be permanently secured to the first anchor 101 at the front of the first anchor 101 such that the attachment ring 103 is in line with the user's tibia and middle of the patella. The attachment ring 103 can be made from a variety of materials including, but not limited to, metals, metal alloys, and hardened plastics. The attachment ring 103 can have a variety of dimensions. According to certain embodiments, the dimensions of the attachment ring 103 are selected such that a strap 111 can be placed through the opening of the attachment ring 103. The attachment ring 103 can have an outer perimeter or circumference in the range of about 0.5 in to about 2 in.

The sock device 100 can also include a sock 110. The sock 110 can have a variety of dimensions and be a "one size fits all" or come in sizes such as small, medium, and large. According to certain embodiments, the length of the sock 110 is selected such that the top of the sock is located at a minimum just below the user's calf muscle and at a maximum just below the bottom edge of the first anchor 101. The sock can be made from a variety of materials. Non-limiting examples of materials include cotton, cotton blends, polyester, microfiber, wool, wool blends, cashmere wool, nylon, spandex, and combinations thereof.

The sock device 100 can also include a second anchor 102. The second anchor 102 can be located at the top of the sock 110. A portion of the second anchor 102 can be permanently affixed to the front or back of the top of the sock. As used herein, "front" means the portion of the sock that is located on and adjacent to the user's tibia when clothed, and "back" means the portion of the sock that is located opposite from the front of the sock. The second anchor 102 can include two strips that extend on both sides from the permanently affixed portion. The two strips can be wrapped around the user's calf muscle after the sock is clothed. The two strips can be removably attached together around the user's lower leg at or near the calf muscle. The two strips can be removably attached together via VELCRO®, a hook and eyes, a button hole and buttons, or snap fasteners as discussed above with reference to the first anchor 101. This second anchor 102 can help keep the top of the sock in the desired position once clothed and prevent or inhibit downward movement of the top of the sock towards the user's ankle.

The sock device 100 can also include a strap 111. A bottom portion of the strap 111 (i.e., the portion located closest to the user's ankle) can be permanently affixed to the sock via a connector 113. The connector 113 can be for example threads or stitching that permanently affixes the strap 111 to the sock 110. A top portion of the strap 111 that is not affixed to the sock 110 can extend from the affixed portion in a direction towards the user's patella when clothed. The segment of the strap 111 can be placed through the attachment ring 103, pulled down towards the user's ankle, and secured to a bottom portion of the strap 111 via attachment of the top portion of the strap to the connector 113 or other portion of the strap 111. According to certain embodiments, the strap is attached via VELCRO®. According to certain other embodiments, the strap 111 is attached via a hook and eyes, a button hole and buttons, or snap fasteners (as discussed above with reference to the first anchor 101).

The first anchor 101, the second anchor 102, and the strap 111 can be made from a variety of materials. According to certain embodiments, the first anchor 101, the second anchor 102, the strap 111, and combinations thereof are made from VELCRO®. According to certain other embodiments, when the securing or attachment means is a hook and eyes or button hole and buttons, then the first and second anchor, the strap, and combinations thereof utilizing the hook and eyes or button hole and buttons are made from materials selected from cotton, cotton blended materials, polyester, microfiber, wool, wool blends, cashmere wool, nylon, spandex, linen, silk, and combinations thereof. If the first anchor 101, the second anchor 102, and the strap 111 are made from a material that could cause irritation to the user's skin due to movement or rubbing, then preferably the side of the anchors and strap that are in contact with the user's skin is lined with a softer material, such as wool, that will not cause irritation to the skin. An end of the first anchor 101, the second anchor 102, and the strap 111 can further include a loop whereby a user can place a finger through the loop in order to separate the ends of the straps from each other when the sock device is no longer desirable to use.

Securement of the strap 111 after the sock 110 is clothed, the first anchor 101 is fixed, and the strap 111 placed through the attachment ring 103 and secured can cause flexing of the user's foot upwards towards the knee. This flexing can cause stretching of the muscles and tendons of the heel region, calf region, and underneath area of the feet. Preferably, the length of the strap 111 is selected such that the user can increase or decrease the amount of flexing of the feet to a desired amount. In this manner, the user can adjust the amount of flexing to both feet, for example the same or different amounts of flexing on each foot, such that a sufficient amount of stretching is provided without causing pain to the user. As the muscles stretch after securing the strap 111, it may be desirable for the user to readjust the strap such that increased flexing is achieved in order to provide increased stretching of the muscles.

Figure 4:
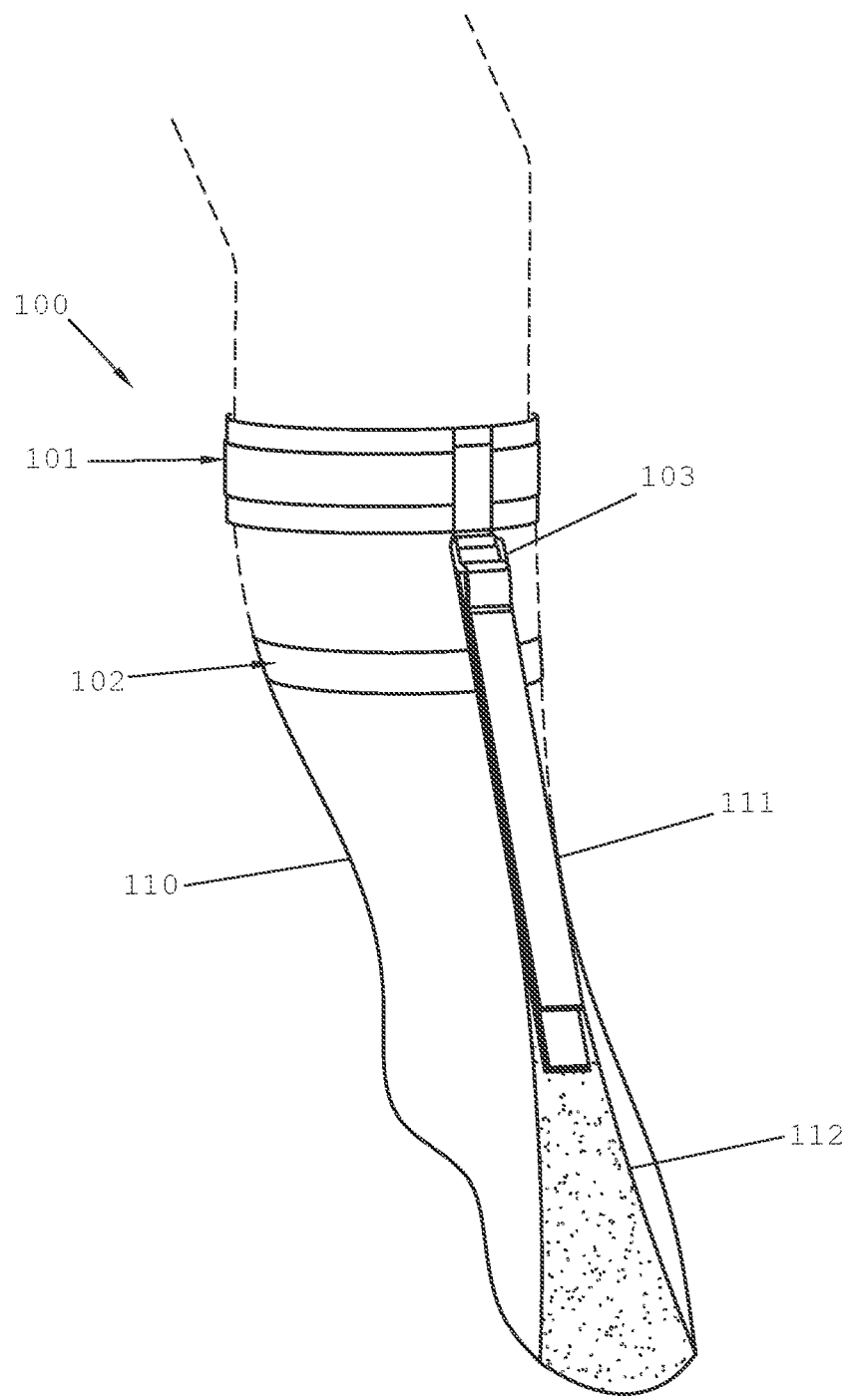
FIG. 4 is a front, side perspective view of the sock device adorned on a wearer.
Figure 5:
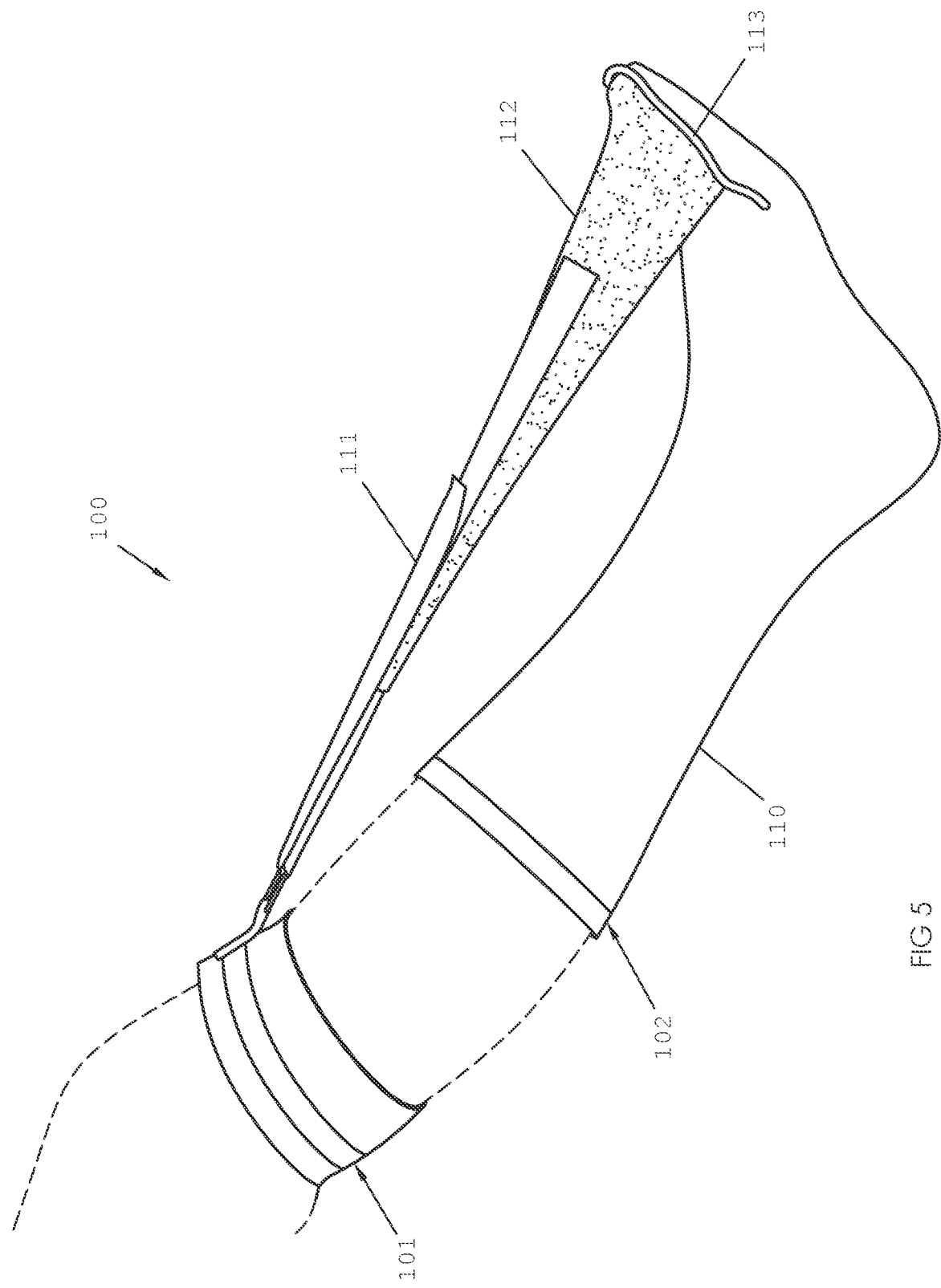
FIG. 5 is a side perspective view of the sock device of FIG. 4 adorned on a wearer.

Unlike other devices for stretching muscles, the sock device 100 can also include a distributor 112. According to certain embodiments and as shown in FIG. 1, the distributor 112 is the bottom portion of the strap 111, wherein the width of the strap 111 located at the toe portion of the sock 110 can be configured to extend the entire width or substantially the entire width of the toe of the sock 110. According to another example, the bottom portion of the strap 111 can be permanently attached (for example via sewing) to the distributor 112, wherein the distributor 112 is made from the same as or different from the material of the sock 110 and wherein the distributor spans the entire or substantially entire width of the toe portion of the sock 110, for example as shown in FIGS. 4 and 5. According to this embodiment, the distributor 112 can be made from a material that is thicker and more rigid than the material the sock 110 is made.

Figure 2A:
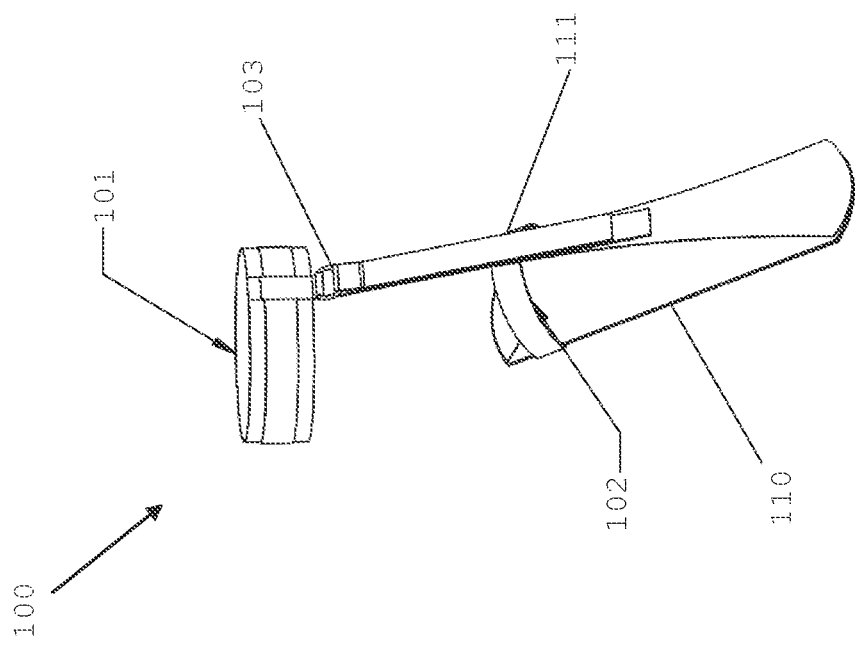
FIG. 2A is a side perspective view of a sock device according to certain other embodiments.
Figure 2B:
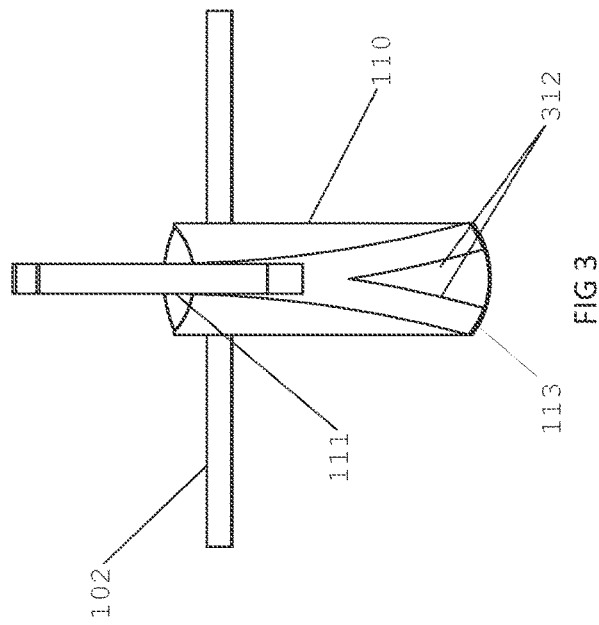
FIG. 2B is a bottom perspective view of the sock device of FIG. 2A.
Figure 2C:
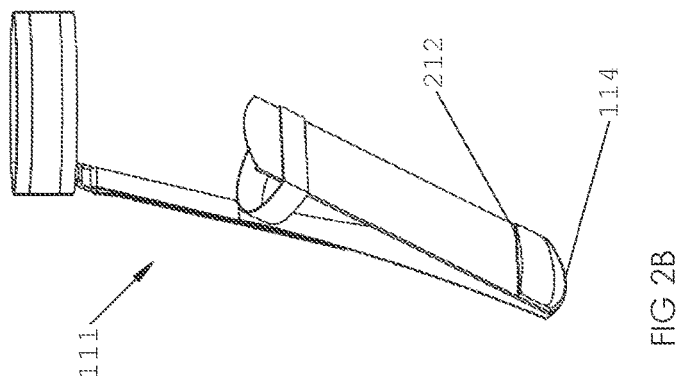
FIG. 2C is a top view of the sock device of FIG. 2A.

According to certain other embodiments and as shown in FIGS. 2A-2C, the underneath side (i.e., the side located underneath the toes of the user's foot) of the toe portion of the sock 110 can include a pocket 114 that spans the entire or substantially entire width of the underneath side of the toe of the sock for receiving the distributor 212. The distributor 212, according to this embodiment, can be a solid piece of material with dimensions selected to fit inside the pocket 114. The material of the distributor 212 can be a rigid material or a semi-flexible material. By way of example, the distributor 212 can be made from plastic. The sock device 100 can include more than one distributor 212 for insertion into the pocket 114. Each of the more than one distributors 212 can be made from different materials that provide a variety of rigidity. In this manner, the user may select a distributor 212 made from a semi-flexible material for use during the day while at work for example and select a distributor made from a rigid material for use while sleeping.

Figure 3:
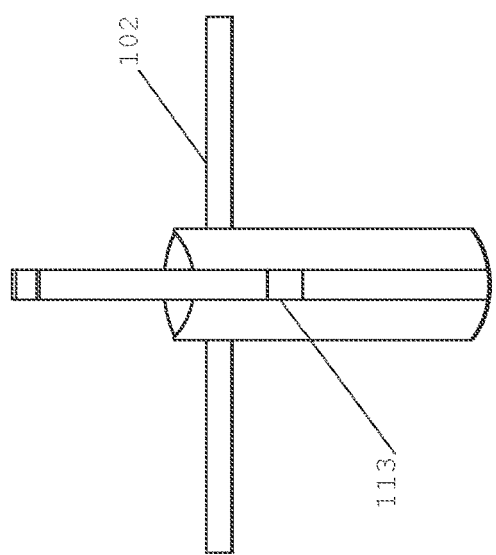
FIG. 3 is a top view of a sock device according to certain other embodiments.

According to yet other certain embodiments and as shown in FIG. 3, the distributor 312 can include two winged portions wherein a first end of each of the winged portions conjoin or come together and connect to a bottom portion of the strap 111 and connector 113. The second ends of the winged portions that are located opposite of the first ends can be permanently attached to: the outermost top portion of the toe portion of the sock; the sides of the toe portion of the sock; or both a top outermost portion and the sides of the toe portion of the sock 110. As used herein, "outermost" means the areas at or near the hallux or "big toe" and the little toe or "outermost toe." As used herein, "top portion" means the portion of the sock that is located on top of the toes as opposed to underneath the toes.

In this manner, during use and flexing of the feet, the force of flexing is distributed across the width of the user's foot by the distributor. It is believed that by distributing the flexing force evenly across the width of a user's foot via the distributor, muscle cramping is reduced, more even stretching the muscles and tendons of the heel region, calf region, and underneath area of the feet is achieved, and improved treatment of plantar fasciitis occurs.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention.

As used herein, the words "comprise," "have," "include," and all grammatical variations thereof are each intended to have an open, non-limiting meaning that does not exclude additional elements or steps. While compositions, systems, and methods are described in terms of "comprising," "containing," or "including" various components or steps, the compositions, systems, and methods also can "consist essentially of" or "consist of" the various components and steps. It should also be understood that, as used herein, "first," "second," and "third," are assigned arbitrarily and are merely intended to differentiate between two or more anchors, etc., as the case may be, and does not indicate any sequence. Furthermore, it is to be understood that the mere use of the word "first" does not require that there be any "second," and the mere use of the word "second" does not require that there be any "third," etc.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A sock device comprising:
   A) a first anchor;
   B) a sock, wherein the sock comprises a toe portion and a heel portion, wherein the sock comprises an upper surface and a lower surface, wherein the lower surface is configured to be located underneath a user's foot when adorned, and wherein the first anchor is indirectly and removably attached to the sock;
   C) a strap, wherein the strap indirectly and removably attaches the first anchor to the sock;
   D) a distributor, wherein the distributor is made from a solid piece of a semi-flexible or rigid material; and
   E) a pocket located on an underneath side of the toe portion of the sock having a width that spans the entire or substantially entire width of the underneath side of the toe portion of the sock, wherein an outside edge of the pocket is permanently and directly attached to the lower surface of the sock to form the pocket having an opening for receiving the distributor, and wherein the pocket has a depth that spans less than half a distance from the heel portion of the sock to the toe portion of the sock,
   wherein the distributor has dimensions selected such that the distributor fits within the pocket, and
   wherein A, B, C, D, and E are separate structures from each other.

2. The sock device according to claim 1, wherein the first anchor comprises an adjustable strap, wherein the adjustable strap is configured to be positionable around the circumference of a user's lower leg at a location below the knee and above the major portion of the calf muscle.

3. The sock device according to claim 2, wherein the first anchor is configured to be secured around the user's lower leg via a first side comprising stiffened hooks and a matingly engagable second side comprising a plurality of soft loop; a hook that is located on a first end of the adjustable strap and a plurality of eyes positioned in a desired spacing pattern located along a second end of the adjustable strap; a button hole located on the first end of the adjustable strap and a plurality of buttons positioned in a desired spacing pattern located along the second end of the adjustable strap; or a male snap fastener located on the first end of the adjustable strap and a plurality of female snap fasteners positioned in a desired spacing pattern located along the second end of the adjustable strap.

4. The sock device according to claim 3, wherein a number of eyes, buttons, or female snap fasteners of the plurality of the eyes, buttons, or female snap fasteners ranges from 3 to 10, and wherein the eyes, buttons, or female snap fasteners are spaced apart at a distance in the range of about 0.5 inches to about 1.5 inches.

5. The sock device according to claim 1, further comprising an attachment ring, wherein the attachment ring is configured to be attached to a front of the first anchor at a position in line with a middle of a user's patella when the sock is clothed and the first anchor is secured around the user's lower leg.

6. The sock device according to claim 5, wherein the attachment ring is made from a material selected from metals, metal alloys, or hardened plastics.

7. The sock device according to claim 1, wherein a length of the sock is selected such that after clothing, a top of the sock is configured to be located between a minimum height and a maximum height along a user's lower leg and below a bottom edge of the first anchor.

8. The sock device according to claim 1, wherein the sock is made from a material selected from the group consisting of cotton, cotton blends, polyester, microfiber, wool, wool blends, cashmere wool, nylon, spandex, and combinations thereof.

9. The sock device according to claim 1, further comprising a second anchor, wherein the second anchor is located at a top of the sock.

10. The sock device according to claim 9, wherein a portion of the second anchor is permanently affixed to a front or back of the top of the sock.

11. The sock device according to claim 10, wherein the second anchor comprises two strips that extend from both sides of the permanently affixed portion, and wherein the two strips are configured to wrap around a user's calf muscle after the sock is clothed and the two strips are secured together.

12. The sock device according to claim 1, wherein a first end of the strap is permanently affixed to a toe portion of the sock via a connector.

13. The sock device according to claim 12, wherein a second end of the strap extends from the first end of the strap in a direction away from a toe of the sock.

14. The sock device according to claim 13, wherein the strap indirectly and removably attaches the first anchor to the sock via placement of the second end of the strap through an attachment ring located on the first anchor and securing the second end of the strap to a bottom portion of the strap.

15. The sock device according to claim 1, wherein the distributor is made from a material that is different from a material of the sock.

16. The sock device according to claim 1, wherein the distributor is made from plastic.

17. The sock device according to claim 1, further comprising a second distributor, wherein the second distributor has dimensions selected such that the second distributor fits within the pocket when the distributor is not located within the pocket.

18. The sock device according to claim 17, wherein the distributor is made from a semi-flexible material and the second distributor is made from a rigid material.

* * * * *